US008788215B2

(12) United States Patent
Chakraborty et al.

(10) Patent No.: US 8,788,215 B2
(45) Date of Patent: *Jul. 22, 2014

(54) METHODS OF ASSOCIATING AN UNKNOWN BIOLOGICAL SPECIMEN WITH A FAMILY

(71) Applicant: The University of Tennessee Research Foundation, Knoxville, TN (US)

(72) Inventors: Ranajit Chakraborty, Fort Worth, TX (US); John Douglas Birdwell, Oak Ridge, TN (US); Tse-Wei Wang, Oak Ridge, TN (US); Dale V. Stansberry, Oak Ridge, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 191 days.

This patent is subject to a terminal disclaimer.

(21) Appl. No.: 13/621,311

(22) Filed: Sep. 17, 2012

(65) Prior Publication Data

US 2013/0030713 A1   Jan. 31, 2013

Related U.S. Application Data

(63) Continuation of application No. 11/467,834, filed on Aug. 28, 2006, now Pat. No. 8,271,201.

(60) Provisional application No. 60/836,941, filed on Aug. 11, 2006.

(51) Int. Cl.
*G01N 33/50* (2006.01)
*G06F 19/18* (2011.01)

(52) U.S. Cl.
CPC .................................. *G06F 19/18* (2013.01)
USPC .......................................................... 702/19

(58) Field of Classification Search
None
See application file for complete search history.

(56) References Cited

U.S. PATENT DOCUMENTS

| | | | |
|---|---|---|---|
| 6,741,983 | B1 | 5/2004 | Birdwell et al. |
| 7,272,612 | B2 | 9/2007 | Birdwell et al. |
| 7,454,411 | B2 | 11/2008 | Birdwell et al. |
| 2003/0232356 | A1 | 12/2003 | Dooley et al. |
| 2004/0126803 | A1 | 7/2004 | Cash et al. |
| 2005/0176031 | A1 | 8/2005 | Sears et al. |

OTHER PUBLICATIONS

R. C. Elston, et al., "A General Model for the Genetic Analysis of Pedigree Data," Human Heredity 21: pp. 523-542, 1971.
Soledad A. Fernandez, et al., "Sampling genotypes in large pedigrees with loops," Genet. Sel. Evol. 33, 2001, pp. 337-367.
Frank Dudbridge, "A survey of current software for linkage analysis," Human Genomics, vol. 1, No. 1, Nov. 2003, pp. 63-65.
C. Cannings, et al., "The Recursive Derivation of Likelihoods on Complex Pedigrees," Advances in Applied Probability, vol. 8, No. 4, Dec. 1976, pp. 622-625.
Eric S. Lander, et al., "Construction of Multilocus Genetic Linkage Maps in Humans," Proceedings of the National Academy of Sciences of the United States of America, vol. 84, No. 8, Apr. 15, 1987, pp. 2363-2367.
Fung, User-friendly programs for easy calculations in paternity testing and kinship determinations, Sep. 2003, Forensic Science International, vol. 136, Issues 1-3, pp. 22-34.
Leclair, Large-scale comparative genotyping and kinship analysis: evolution in its use for human identification in mass fatality incidents and missing persons databasing, Apr. 2004, International Congress Series, vol. 1261, pp. 42-44.
B. Leclair et al., Application of Automation and Information Systems to Forensic Genetic Specimen Processing, Future Drugs Ltd., Mar. 2005, pp. 241-250.
K. L. Monson et al., The mtDNA Population Database: An Integrated Software and Database Resource for Forensic Comparison, Forensic Science Communications, Apr. 2002, pp. 1-6.
F. V. Jensen et al., Bayesian Updating in Causal Probabilistic Networks by Local Computations, Computational Statistics Quarterly, 1990, pp. 269-282.
S. M. Edson et al., Naming the Dead—Confronting the Realities of Rapid Identification of Degraded Skelatal Remains, Central Police University Press, 2004, pp. 64-89.
D. J. Spiegelhalter et al., Statistical Reasoning and Learning in Knowledge-bases Represented as Causal Networks, Springer-Verlag, 1988, pp. 105-112.
L. Roewar et al., Online Reference Database of European Y-Chromosomal Short Tandem Repeat (STR) Halotypes, Forensic Science International, 2001, pp. 106-113.
Frederick R. Bieber et al., Finding Criminals Through DNA of Their Relatives, Science, Jun. 2, 2006, p. 1315-1316.
Author Unknown, DNAVIEW2 2006 User's Manual, Apr. 28, 2006, version 27.49, pp. 1-328.
Leslie G. Biesecker et al., DNA Identification After the 9/11 World Trade Center Attack, Science Magazine, Nov. 18, 2005, pp. 1122-1123, vol. 310, American Association for the Advancement of Science.
Charles H. Brenner, Some Mathematical Problems in the DNA Identification of Victims in the 2004 Tsunami and Similar Mass Fatalities, Forensic Science International, Dec. 19, 2005, pp. 172-180, vol. 157, Elsevior.

(Continued)

*Primary Examiner* — Jason Sims
(74) *Attorney, Agent, or Firm* — Cameron LLP

(57) ABSTRACT

The present invention provides a method of predicting whether an unknown biological specimen originates from a member of a particular family. The method compares DNA profiles from at least one unknown biological specimen to DNA profiles of more than one family member, which significantly increases the methods' predictive ability. In particular, the invention describes a method of comparing test DNA profiles from unknown biological specimens to a family pedigree comprising target DNA profiles obtained from biological specimens of family members. In one embodiment, a modified Elston Stewart algorithm is used to determine a probability that a genetic relationship exists between at least one unknown biological specimen and the family pedigree.

40 Claims, 4 Drawing Sheets

(56) References Cited

OTHER PUBLICATIONS

Charles H. Brenner, Symbolic Kinship Program, Genetics, Feb. 1997, pp. 535-542, vol. 145, Genetics Society of America.

Charles H. Brenner and B. S. Weir, Issues and Strategies in the DNA Identification of World Trade Center Victims, Theoretical Population Biology, 2003, pp. 173-178, vol. 63, Elsevier.

Howard D. Cash et al., Development Under Extreme Conditions: Forensic Bioinformatics in the Wake of the World Trade Center Disaster, Pacific Symposium on Biocomputing, 2003, pp. 638-653, Stanford University.

Leonid Kruglyak et al., Parametric and Nonparametric Linkage Analysis, American Journal of Human Genetics, 1996, pp. 1347-1363, vol. 58, The American Society of Human Genetics.

Dale R. Nyholt, All LODs Are Not Created Equal, American Journal of Human Genetics, 2000, pp. 282-282, vol. 67, The American Society of Human Genetics.

METHODS OF ASSOCIATING AN UNKNOWN BIOLOGICAL SPECIMEN WITH A FAMILY

This application is a continuation of U.S. patent application Ser. No. 11/467,834 filed Aug. 28, 2006 (now allowed) and claims the benefit of U.S. Provisional Application Ser. No. 60/836,941 filed Aug. 11, 2006, which applications are incorporated by reference as to their entire contents.

TECHNICAL FIELD OF THE INVENTION

The technical field of the present invention relates to methods of searching for, ranking, and identifying missing individuals using DNA profiles and DNA database search techniques.

BACKGROUND OF THE INVENTION

Identification of a biological sample using DNA profiles is an important task in forensic science. For example, the terrorist attacks of Sep. 11, 2001 placed huge demands on forensic scientists to identify human remains from the collapsed World Trade Center buildings. In light of these demands, forensic scientists need more efficient and more accurate search methods to assist in identifying biological specimens by using DNA profiling technology.

Ideally, a forensic scientist obtains a DNA profile from a sample obtained from a personal effect of a missing person such as a toothbrush, razor, or comb, and searches for a match in a database containing DNA profiles from unknown biological specimens of a missing person or victim's remains. In theory, this approach can identify the missing person, but in practice, this approach breaks down when it encounters samples with partial profiles or when the reference origin of the personal effect cannot be obtained or verified. It is common to obtain incomplete DNA profiles from disaster areas due to harsh environmental conditions where the DNA integrity has diminished. This forces forensic scientists to lower the match stringencies within database search engines, yielding potentially numerous false positives. In addition, incorrectly labeled personal effects can lead to inaccurate identifications.

When direct searching fails, identification using kinship analysis is often necessary. Kinship analysis comprises possibly narrowing the scope of a search by using any available DNA or non-DNA information to exclude unrelated specimens and then calculating genetic relatedness to at least one biological relative of a missing person. Current technology relies on pairwise comparison of a test DNA profile from an unknown biological specimen to a target DNA profile from a known biological relative, taking into account various familial relationships such as parent-child, sibling or half-sibling, and calculating the value of a function that indicates the likelihood or probability that the relationship is true (e.g., Cash et al., genecodesforensics.com/news CashHoyleSutton.pdf, 2003). A likelihood ratio is commonly used, which indicates the likelihood that the given DNA profiles of the two samples would be obtained if they are related, relative to the likelihood or probability that these DNA profiles would be present if the individuals were unrelated. A measure of genetic similarity can also be used to indicate the likelihood that a relationship is true. Such a measure can for example, account for shared DNA alleles, loss of genetic information through degradation of the DNA, or the possibility of mutation of an allele. For any of these functions, the specimens are then independently sorted according to the function's value. When a likelihood function, such as probability, likelihood, or likelihood ratio is used, the specimens are sorted according to the calculated likelihood function value that the DNA profile from an unknown biological specimen is related to the DNA profile from a biological relative. Unfortunately, this approach is cumbersome and imprecise for large cases, such as the World Trade Center disaster, because each search is for a specimen which is related to a single family member. A pairwise comparison to the DNA profile of a single known relative can produce a large collection of candidate profiles. Human analysts must then sort, correlate, and analyze the matches, possibly manually with available meta data, which is a very labor intensive and time consuming process.

Software tools exist which allow the correlation of DNA match results from a single type of DNA profile, such as short tandem repeat (STR), single nucleotide polymorphism (SNP), or restriction fragment length polymorphism (RFLP), among others. However, these tools do not allow a correlation of DNA match results across multiple types of DNA profiles. Even within one DNA type, for instance, the STR DNA type, searching and matching a missing person candidate's profile against the collective of multiple biological family relatives from the same family pedigree is not possible. Thus, technologies are needed which can use all available DNA profile information involving a missing individual or an unknown biological specimen and his/her relatives to further enhance the ability to make an accurate identification.

SUMMARY OF INVENTION

Several embodiments are discussed herein which provide methods of associating an unknown biological specimen with a particular family. In one embodiment, an unknown biological specimen is identified as likely related to a family of at least a first and second family member. At least a first family member list and a second family member list are combined to create a combined list. The first family member list comprises a set of unknown biological specimens rank-ordered according to a calculated likelihood that a genetic relationship exists between test DNA profiles obtained from a set of unknown biological specimens and a first target DNA profile obtained from a biological specimen of a first family member. The second family member list comprises the set of unknown biological specimens rank-ordered according to a calculated likelihood that a genetic relationship exists between test DNA profiles obtained from the set of unknown biological specimens and a second target DNA profile obtained from a biological specimen of a second family member. The unknown biological specimen with high ranking in the combined list is more likely related to the family In another embodiment, at least one test DNA profile from a set of unknown biological specimens is compared to a family pedigree comprising target DNA profiles obtained from biological specimens of family members. A probability or likelihood that a genetic relationship exists between at least one unknown biological specimen and the family pedigree is calculated using an adapted Elston Stewart algorithm.

In another embodiment, a first DNA profile from a first unknown biological specimen is compared to a second DNA profile from either a second unknown biological specimen or a known biological specimen. A likelihood function value that a genetic relationship exists between the first and the second biological specimen is calculated. A first directed graph, which represents the probability or likelihood that a genetic relationship exists between the first and second unknown biological specimens, is created according to the calculated value of the probability/likelihood function of the relationship. The first directed graph may also represent known or likely genetic relationships between known individuals or between known individuals and unknown biological samples. The First directed graph is compared to a second directed graph, which represents the strength of the known or likely relationships among the members of a family. At least one unknown biological specimen is identified as likely related to at least one member of the family if a portion of the structure of the first directed graph that contains the unknown biological specimen matches a portion of the the structure of the second directed graph.

Other embodiments of the invention are computer-readable media which store computer-executable instructions for performing any of the disclosed methods.

BRIEF DESCRIPTION OF THE DRAWINGS

The present invention is illustrated by way of example, and not by way of limitation, in the figures of the accompanying drawings.

DETAILED DESCRIPTION OF INVENTION

Figure 1:
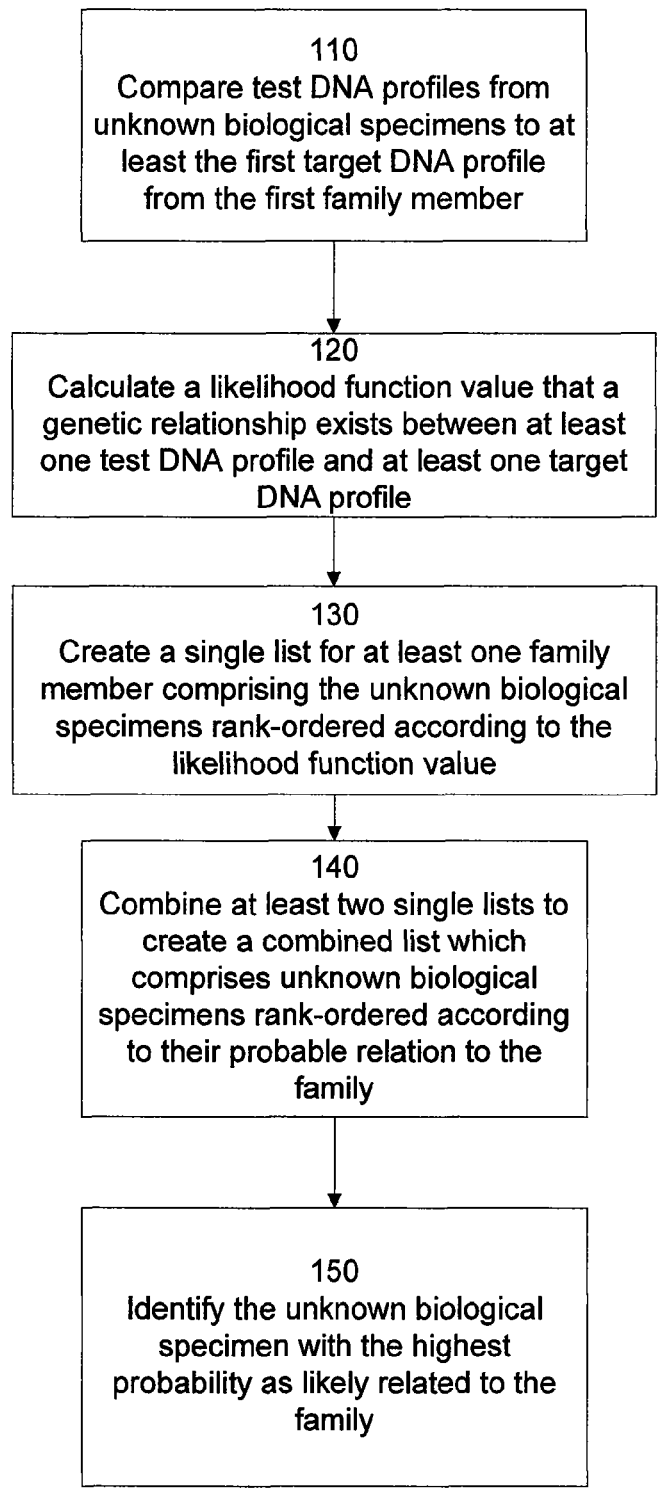
FIG. 1 is a flow diagram that illustrates an overview of one embodiment of a method of identifying an unknown biological specimen as likely related to a family comprising at least a first and second family member.

Referring to FIGS. 1-4, here will now be described several embodiments of methods of predicting whether an unknown biological specimen from an individual originates from a member of a particular family. The individual can be deceased or can be living but unidentified. Methods of the invention use as much available DNA profile information as possible and permit a forensic investigator to identify an unknown biological specimen by ranking test DNA profiles from unknown biological specimen according to a calculated probability, likelihood, likelihood ratio, or a likelihood function value that the test DNA profile is related to target DNA profiles from family members of the missing individual. If an unknown biological specimen is related to more than one target family member, this indicates an increased likelihood (or probability) of a relationship between the unknown biological specimen and the family.

Methods of the invention typically are used with humans but can also be used for any type of individuals which can be grouped into a family. A "family" according to the invention is a group of individuals with common ancestry. A mother, father, grandfather, grandmother, full or half siblings are examples of members of a family, as are cousins, aunts and nephews, and other individuals having a common ancestor. The corresponding missing individual is also a member of the family. Genetic relationships exist within a family according to the Mendelian laws of inheritance. When one calculates a likelihood or likelihood ratio, one takes into account specific, or stipulated genetic relationships such as parent-child, siblings, etc. For example, half of the genetic information contained in a father's nuclear DNA (other than the Y chromosome) will be inherited by a child. Only ¼ of the genetic information contained in a grandfather's nuclear DNA (other than the Y chromosome) will be inherited by his grandchild. All of a mother's mitochondrial DNA will be inherited by her child. All of a father's nuclear DNA from the Y chromosome will be inherited only by his son. The inheritance of both nuclear and mitochondrial DNA may be influenced by mutations. The present invention exploits these genetic relationships to identify an unknown biological specimen as having a probable or likely genetic relationship to the typed genotypes of members of a family.

Suitable families include those of vertebrates, most particularly mammals, including primates (e.g., gorillas, chimpanzees, baboons, squirrel monkeys, humans), companion animals (e.g., cats, rabbits, dogs, horses), farm animals (e.g., cows, sheep, swine, goats, horses), wild animals (e.g., lions, tigers, elephants), and research animals (e.g., eats, dogs, guinea pigs, rabbits, sheep, goats, swine, chimpanzees, mice, rats, and baboons).

The methods' power is based in part on comparison of DNA profiles from unknown biological specimens to DNA profiles of more than one family member, which significantly increases the methods' predictive ability. A "DNA profile" according to the invention comprises one or more DNA markers which together uniquely characterize(s) an individual with high probability and which contain inherited genetic information. A DNA profile can be from one or more of the following DNA types, which correspond to both the source of the DNA and the laboratory process used to obtain the information: single nucleotide polymorphism (SNP), autosomal short tandem repeat (SIR), mitochondrial DNA (mtDNA), mini-STR, or STR DNA from the Y chromosome (Y-STR). In the future, additional DNA types will most likely be developed, and since the methods disclosed herein rely upon the Mendelian laws of inheritance and the mathematics of probability rather than a specific DNA typing technology, these methods will also apply to any newly discovered DNA types. A DNA profile typically contains one or more DNA markers (e.g., 1, 2, 3, 4, 5, 6, 7, 8, 9, 10, 11, 12, 13, 14, 15, or more), which can be of various types. For example, polymorphic SIR loci which can be included in a DNA profile include D3S1358, vWA, FGA, D8S1179, D21S11, D18S51, D5S818, D13S317, D7S820, D16S539, THO1, TPDX, CSF1PO, Penta D, Penta E, D19S433, and AMEL.

DNA profiles for use in methods of the invention are obtained from biological specimens. A "test DNA profile" according to the invention is a DNA profile obtained from an unknown biological specimen or an individual with a questioned relationship. A "target DNA profile" according to the invention is a DNA profile obtained from a biological specimen of a personal effect of a missing person or a known family member. A "biological specimen" according to the invention is a sample from which DNA can be obtained. Suitable samples include, but are not limited to, nucleated blood cells, bones or bone fragments, skin cells, hair, saliva, cells obtained from a cheek swab, and DNA remaining on a personal effect, such as a toothbrush, bedding, a razor, a glass used for drinking, a cigarette butt, or a hairbrush. An unknown biological specimen can be derived from living tissue (e.g., a biopsy) or from deceased tissue (e.g., a remain), bone fragments, hair, or fingernail scrapings.

One can extract DNA from an unknown biological specimen by using any DNA extraction technique. Many techniques for extracting DNA are well known in the art. See, e.g., Gurvitz et al. Australas Biotechnol. 1994 March-April; 4(2): 88-91; Ma et al. J Forensic Sci Soc. 1994 October-December; 34(4):231-5; Laber et al. J Forensic Sci. 1992 March; 37(2):

404-24. Methods of obtaining DNA profiles from the extracted DNA are well known in the art and include, but are not limited to, DNA sequencing, restriction digestion, polymerase chain reaction, and microarray analysis.

Referring to FIG. 1, in one embodiment, an unknown biological specimen is identified as likely related to a family of at least two family members by its position in a rank-ordered "combined list." The combined list 140 comprises two or more family member lists. A "family member list" 130 comprises a set of unknown biological specimens rank-ordered according to a calculated likelihood function value that a genetic relationship of a specific type exists between test DNA profiles obtained from the set of unknown biological specimens and a target DNA profile obtained from a biological specimen of a family member. The combined list comprises the set of unknown biological specimens rank-ordered according to a calculated probability/likelihood that a genetic relationship exists between test DNA profiles and target DNA profiles from at least two family members. A highly ranked unknown biological specimen is identified as likely related to the family.

One embodiment of the present invention involves searching at least one database containing test DNA profiles derived from unknown biological specimens and comparing these profiles to target DNA profiles from known family members. Test DNA profiles may all be of one type (e.g., a set of short tandem repeats; STR DNA) or there may be multiple types of test DNA profiles for one or more samples. Test DNA profiles can be stored in a database according to profile type, or a single database may store DNA profiles having information about multiple DNA profile types. For example, STR test DNA profiles may be stored in a STR test DNA profile database and mitochondrial test DNA profiles may be stored in a corresponding mitochondrial test DNA profile database.

In block 110, the comparison can be made manually but use of a computer is preferred. Thus, a database preferably contains a search engine which implements search, match, and retrieval methods for a particular test DNA profile type. Search engines preferably are both efficient and scale sublinearly (e.g., logarithmically) with database size.

In block 120, a probability or likelihood that a genetic relationship exists can be determined by a variety of methods. The likelihood that a relationship exists between a test DNA profile from an unknown biological specimen and target DNA profile from a family member can be evaluated mathematically. For example, an unknown profile cannot be excluded as a child of a DNA typed parent if the unknown biological sample has at least one STR allele in common with the parent at each locus. For other family members, one uses likelihood ratios or a likelihood function for this determination, but other evaluation methods can be used, such as expert systems or heuristic rules. A probability, in this sense, is defined as the mathematical chance that a given genetic profile is observed for the test profile conditioned on the genetic profiles observed for the relatives under the hypothetical biological relationship. Note that the hypothetical relationship may be in the usual sense of a relationship between two members of a family, or it may be the hypothesis that a relationship does not exist or can not be determined. Probability is expressed as a number between zero and one. Zero means that it is impossible to observe the test profile under the hypothetical relationship, and one implies that the test profile would be observed with certainty under the hypothetical relationship and the observed profile of the family member(s). A likelihood is defined as the reciprocal of a probability. A "likelihood ratio" is defined as a ratio of two probabilities. The probability of the observation of a set of profiles under the assumption that the specimens are related divided by the probability of the same set of profiles under the assumption that the specimens are not related would be one example of a likelihood ratio. The relationship may be between two specimens, or between a specimen and specimens associated by members of a family pedigree, possibly including missing persons. In any of these embodiments, a probability may be replaced by another measure of the possibility or likelihood, or a likelihood function of a relationship. A "likelihood function" according to this invention comprises any probability, likelihood, or likelihood ratio calculation that evaluates the degree of manifestation of a genetic relationship between at least two DNA profiles, biological specimens, graphs, or possibly anything which represents an individual or a family.

"Filtering", as defined in these embodiments is the exclusion of specimen, or DNA profiles that are not compatible with a family pedigree, or possibly additional information, based upon either DNA or non-DNA information. A "family pedigree" comprises information about the members of a family, where the family may include biological specimens, individuals, or missing persons and the information can be DNA information or non-DNA information, and information, either explicit or implicit, that describes the relationships among the members of a family. Filtering, or excluding also refers to narrowing or limiting potential search results. It is desirable to perform such filtering using efficient database search methods. The methods described in U.S. Pat. No. 6,741,983 and U.S. Pat. No. 7,272,612 are suitable for DNA information. Efficient database search methods are well-known for non-DNA information. A database may be parallelized in order to enhance performance and/or scalability, as described in U.S. Pat. No. 7,454,411.

For example, if in a family pedigree comprising a father, mother, and two children, typed STR DNA is available for the father, and a child is missing, a search of a database of unidentified human remains can be performed to return all specimens having DNA profiles that are compatible with the father's SIR DNA profile. In this case, STR DNA profiles are classified as compatible when at least one allele is shared by the father and child at each SIR DNA locus, except for loci of the Y chromosome, in which case all Y-STR DNA alleles are shared if the child is male. If for example, within a family pedigree, mtDNA is available for a mother or a relative sharing the same maternal lineage, then a search could be performed to return all specimen having mtDNA profiles that match the mtDNA of the typed mother or the maternally linked relative. Additionally, non-DNA forensic information can be used, for example, to exclude samples from remains found before the last date and time the child was seen. The benefit of using a search to filter or exclude specimens is that one has the ability to use an efficient database search method to rapidly prune the size of the population of specimens that must be further analyzed and ranked using, for example, a likelihood function, which may be less efficient than database search.

Once the probabilities or likelihoods of genetic relationships between unknown biological specimens and family members are evaluated, the unknown biological specimens are rank-ordered according to the likelihood value of being related to a family member. A family member list 130 can be created for at least one family member; the family member list contains unknown biological specimens listed in order of their likely relationship to the family member. At least two single lists from different family members are then combined into one combined list 140. For example, family member lists from a mother, father, or grandfather can be combined into one combined list 140 which represents the list for the family.

Lists can be combined by summing, averaging, or using other mathematical operations to merge data from at least two lists into one combined list. Such combining can be accomplished by performing mathematical operations on the likelihood function values used to order the biological specimens of each list, by performing mathematical operations on the positions or relative positions of the biological specimens of each list, or by a combination of these methods. It can be desirable to exclude unknown biological specimen from a combined list if the specimen can be excluded from one of the family member lists. It can also be desirable to exclude unknown biological specimen from a list if the specimen has been identified. In block 150, the top few highest-ranked unknown biological specimens in the combined list contain the unknown biological specimen that is most likely the correct missing person for this family. More generally, the unknown biological specimen that corresponds to a specified missing person is likely to be highly ranked.

Figure 2:
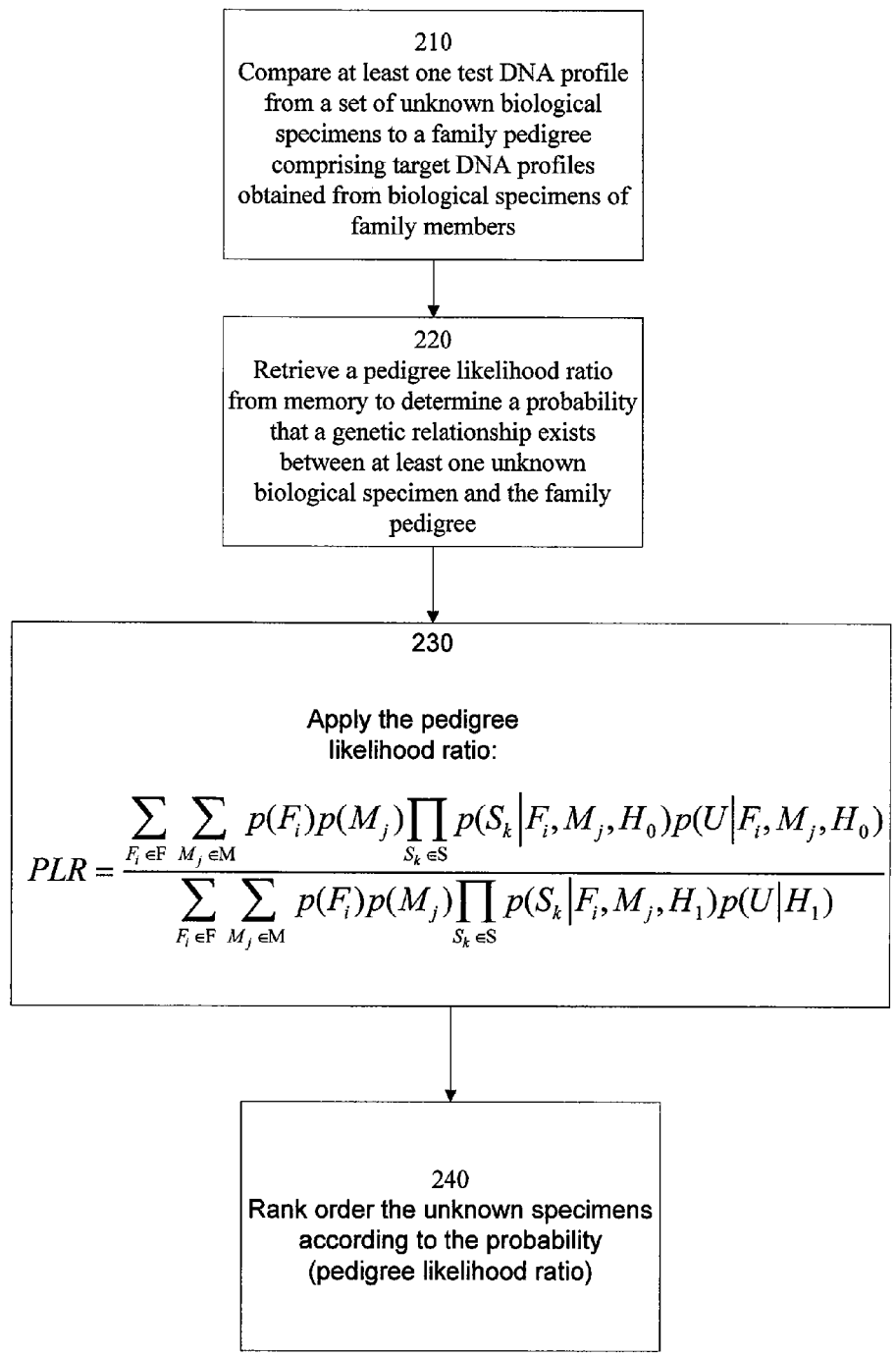
FIG. 2 is a flow diagram that illustrates an overview of one embodiment of a method of identifying an unknown biological specimen as likely related to a family comprising at least a first and second family member.

In another embodiment, referring to FIG. 2, when multiple genetically related family members are available to donate their DNA, the DNA should be used jointly and simultaneously to derive a joint likelihood ratio, or pedigree likelihood ratio (PLR). This PLR between the missing person/victim and the family pedigree is derived under the hypothesis that the missing person is related in the stipulated manner to the family pedigree, against the hypothesis that he/she is unrelated to the family pedigree. For a family pedigree under consideration, the PLR for each potential missing person candidate is to be calculated, and the missing person candidates are then ranked according to the PLR. The top ranked candidates should contain the correct missing person sought after by the family corresponding to this family pedigree. Mathematically, the more members of a family pedigree that are available or the closer they are related to the missing person, the more precise and effective the ranking will be. PLR is based on the set of available genotype information of the multiple family members, explicitly incorporating into its calculation the known relationships among the family members and the putative relationship to the missing person candidate.

Figure 4:
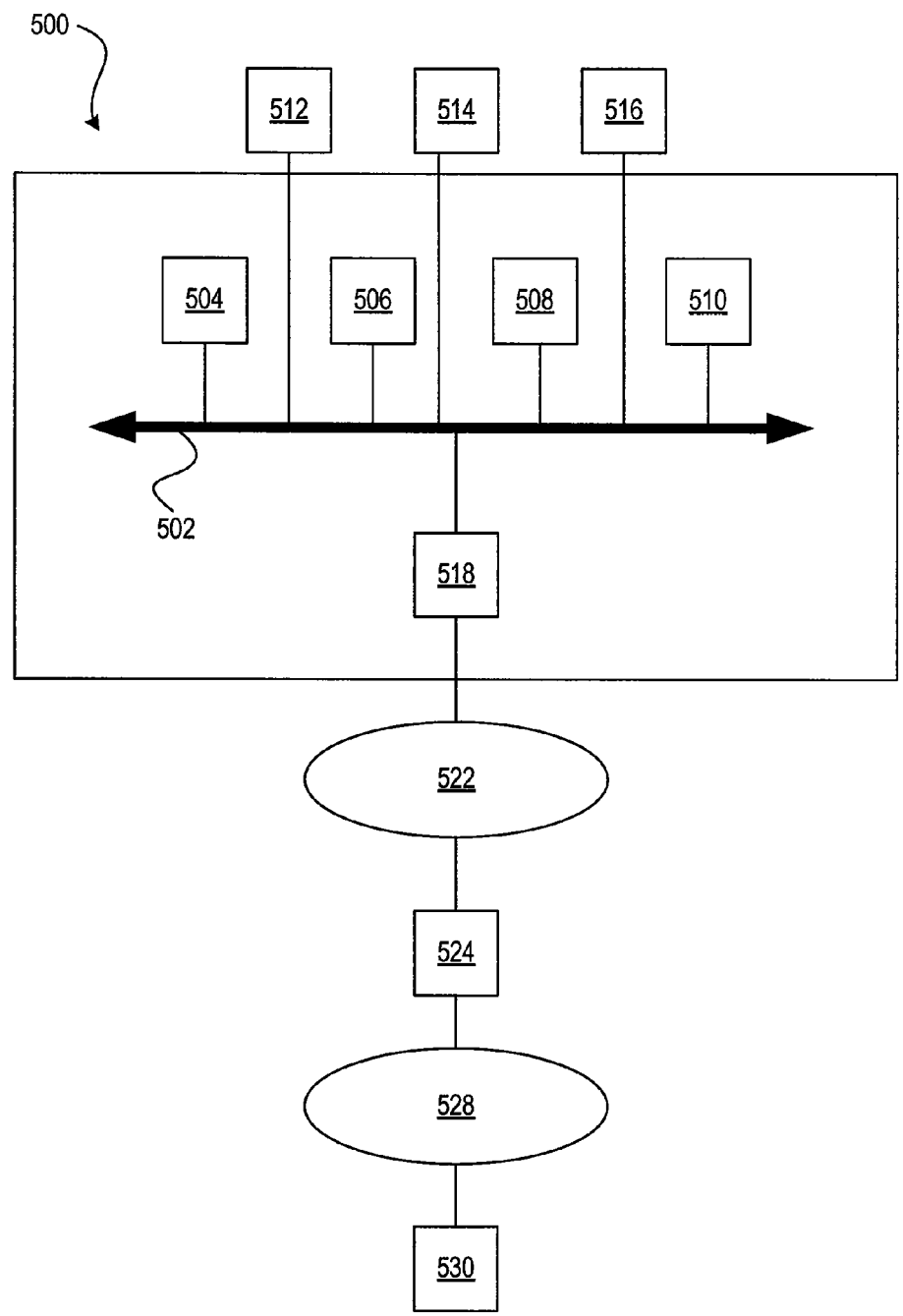
FIG. 4 illustrates a block diagram of a hardware environment that may be used according to an illustrative embodiment of the invention.

In this embodiment, referring to FIG. 2, relationships between multiple known target DNA profiles from a family which are described by a family pedigree are used to evaluate the likelihood that the unknown specimen is from the missing person related to the family. In this embodiment, in block 210, a test DNA profile from at least one unknown biological specimen is compared to the genetic information of the family pedigree which comprises target DNA profiles obtained from biological specimens of at least two family members. The comparison can be made manually or with the aid of a computer. In block 220, a modified Elston Stewart algorithm can be retrieved from computer memory as shown in FIG. 4 for calculating a pedigree likelihood ratio that a genetic relationship exists between at least one unknown biological specimen and the members of the family pedigree. In block 230, a modified Elston Stewart algorithm accomplishes this mathematical evaluation by providing a pedigree likelihood ratio that a test DNA profile from an unknown biological specimen has a genetic relationship of a specific type to a family pedigree.

The original Elston Stewart algorithm (Elston and Stewart 1971) includes a penetrance term expressing the probability of phenotypic expression of a disease if the individual hears the genotypic disease marker. It also includes a probability measure for the degree of linkage of markers residing at different loci. The Elston and Stewart algorithm was adapted to use the penetrance term instead to represent the probability of mutation at an allele that occurs during meiosis from a parent to child lineage inheritance event, if occurrence of mutation is to be considererd. If mutation occurrence is not to be considered, then the penetrance term is set to 1. In addition, the term that expresses a linked relationship between markers residing at different genetic loci is not used. The original algorithm is adapted to accommodate the assumption of independence of marker alleles residing at different loci, although should an assumption of independence of marker alleles not be valid for some future DNA type adopted by the forensics community, the term that expresses a linked relationship can be re-inserted in the algorithm. An example mathematical equation for this pedigree likelihood ratio, without considering mutational occurrence, for a family pedigree comprised of a father, mother, and sibling(s), where either the father, mother, or both can be genetically untyped is $$PLR = \frac{\sum_{F_i \in F} \sum_{M_j \in M} p(F_i) p(M_j) \prod_{S_k \in S} p(S_k \mid F_i, M_j, H_0) p(U \mid F_i, M_j, H_0)}{\sum_{F_i \in F} \sum_{M_j \in M} p(F_i) p(M_j) \prod_{S_k \in S} p(S_k \mid F_i, M_j, H_1) p(U \mid H_1)}$$

where F and M are the sets of possible DNA profiles for the father and mother, respectively, S is the set of DNA profiles for typed siblings, and U is the DNA profile for the unidentified human remain. $H_0$ is the hypothesis that the unidentified human remain is from a missing child in this family pedigree, and $H_1$ is the hypothesis that there is no known relationship between the unidentified human remain and the family pedigree. This equation is one example PLR for this family pedigree. Equations for family pedigrees comprised of different combinations of family members can be written using the same adaptation to the Elston Stewart algorithm or similar published works, such as those by E, Lander and P. Green (Lander and Green 1987) or by C. Cannings, E. Thompson, and E. Skolnick (Cannings et al. 1976) and others (Dudbridge F. 2003; Fernandez et al. 2001).

A PLR can be evaluated in different ways. For example, a straightforward way to evaluate the above equation is to enumerate all possible unknown profiles and multiply and sum over these enumerated unknown profiles the probabilities and conditional probabilities that depend upon them. Simplifications can by used when the profile of either the father or the mother, or both, is known. Many loci are independent from each other, and in this case a term can be calculated tier each independent locus, and the product of these terms can then be incorporated in the PLR. Another way is to consider the number of alleles or genotypes that are inherited by a child from one or both parents and use a probability or conditional probability that this number has occurred. This is known as "identical by descent" (IBD), and in this case the terms of the PLR are grouped according to the number of alleles or genotypes IBD. A calculation using an IBD approach can consider IBD alleles between any two genetically related biological specimens or individuals; it is not restricted to parent/child relationships. Alternatively, portions of the equation for the PLR may be pre-computed. This can be especially beneficial when the PLR is to be calculated for a number of unknown human remains; for example, the product terms over all known siblings may be pre-computed. Another way is to predetermine a sequence of machine instructions that can be executed to calculate the PLR for a given family pedigree in a highly efficient manner, and then execute these instructions for each of a set of unknown human remains. Finally, if the family pedigree incorporates multiple generations, the PLR may be computed in a recursive manner, in either a bottom-up or top-down fashion. The family pedigree may contain loops, in which case the approach of C. Cannings, E. Thompson, and E. Skolnick, or a similar approach, may be employed.

Pedigree likelihood ratios, as described above, can be used to evaluate whether there is a reasonable degree of certainty that an identification determined in this manner is correct. Optionally, as shown in block 240, the unknown biological specimens can be rank-ordered according to a pedigree likelihood ratio that at least one unknown biological specimen is related to the family or family pedigree. Higher-ranked unknown biological specimens are more likely to be candidates for the correct missing family member sought by the family represented by the family pedigree.

Figure 3:
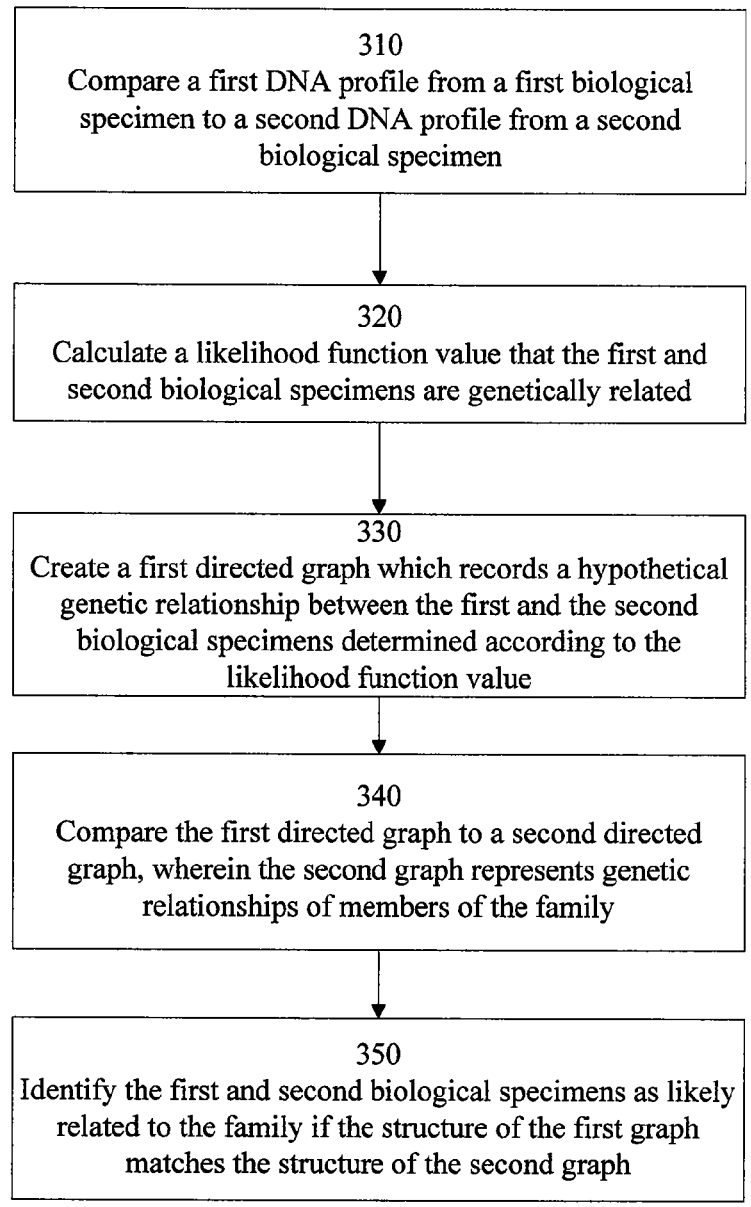
FIG. 3 is a flow diagram that illustrates an overview of one embodiment of a method of identifying at least two unknown biological specimens as likely related to a family comprising at least a first and second family member.

Another embodiment of the invention, referring to FIG. 3, takes advantage of known or hypothetical relationships between biological specimens. This embodiment is particularly suitable to large-scale mass disaster or terrorist incidents where several related members of families are missing or among the victims, such as occur in airline disasters and natural disasters such as tsunamis. A database of DNA profile data from both known and unknown biological specimens can have hypothetical relationships between specimens, some of which may be known to be true, for example, samples taken from various portions of an unidentified remain, and samples from known or related sources. Hypothetical relationships may be based upon, for example, additional forensic evidence linking unidentified remains. Hypothetical relationships can also be tested using standard methods such as likelihood functions or maximum likelihood identification that provide a quantitative measure of the potential validity of each hypothesis. Discovered relationships are hypothetical relationships having a high degree of correctness, and may be based upon, for example, non-DNA forensic information (see below) or mathematical analysis such as the use of likelihood functions or maximum likelihood identification and a decision process whereby a hypothesis of relatedness is accepted and recorded or discarded. One possible decision process is comparison of the value of a a likelihood function to a numeric threshold and acceptance if the value is greater than the threshold.

To determine whether a relationship may exist between two biological specimens (known or unknown), block 310, a DNA profile from one biological specimen is compared to a DNA profile from another biological specimen to determine the probability or likelihood that a genetic relationship exists. Such a relationship can be called a hypothetical relationship. The comparison can be carried out by calculation of the value of a likelihood function and comparison of the value to a threshold. A second approach is to use maximum likelihood estimation or to compute the joint conditional probability of occurrence of the two DNA profiles for a set of hypothetical relationships, and accepting and recording one or more of the relationships having greatest likelihood or probability as having support from the available information. Once two biological specimens are compared, a likelihood of a hypothetical relationship between the two specimens is calculated as described above and shown in block 320. It is important to recognize that multiple hypothetical relationships between two specimens may be accepted for recording, and that each specimen may have accepted relationships with zero, one, or more other specimens. In this context, "accepted for recording" means that the evidence for the relationship, for example based upon forensic evidence or calculated likelihood, is sufficiently strong to indicate that the possibility of this relationship should be recorded, or maintained, for example, in a database for further evaluation or analysis. Each hypothetical or known relationship between the biological specimens can be represented, or recorded, as an edge of a directed graph 330. The term "recorded" is used in these embodiments to show that a relationship has been represented by an edge of a directed graph. A directed graph, as defined in the field of computer science, contains nodes which correspond to specific data and edges which correspond to relationships among the data. An edge has a direction from one node to another, and this edge can represent a dependence of one node upon another, such as "node A is a child of node B". The term "directed graph" is used here to indicate that such dependencies can be represented; however, other methods of representing such dependencies are known in the art such as entity-relationship diagrams or relations between records in tables of a relationship database. Therefore, the term "directed graph" is defined to mean any representation of entities or objects, such as are needed to represent biological specimens, DNA profiles, or individuals, and relationships between these entities or objects that are not necessarily reflexive, meaning, for example, that "node A is a child of node B" does not imply that "node B is a child of node A". Information may be associated with any node or edge to more completely describe the data or relationship. In these methods, nodes of the directed graph correspond to individual biological specimens and/or their DNA profiles, and edges of the directed graph correspond to known or hypothetical and accepted genetic relationships between the biological specimens. In block 340, a family pedigree comprising relationships among family members can also be represented as a directed graph.

In this embodiment, a directed graph that represents a hypothetical or known relationship between biological specimens or individuals and/or the corresponding test DNA profiles is compared to a directed graph that represents a family pedigree defining relationships between individuals (known or missing). The objective of the comparison is to identify portions of the directed graph that represent hypothetical or known relationships between biological specimens or individuals and/or the corresponding test DNA profiles that at least partially correspond to the structure and information specified by the directed graph that represents a family pedigree. The comparison, as shown in block 340, can involve the structure of the directed graph in addition to the DNA profile information contained in the directed graph. For example, the directed graph that represents a family pedigree may describe parent and child relationships of a family, where many families are missing due to a mass disaster, such as occurred subsequent to the Southeast Asian/Pacific tsunami of 2005. Such a comparison may yield many possible matches, corresponding to multiple missing families. If additional known information is included in the directed graph of the family pedigree and its associated data (such as DNA profiles of known individuals or non-DNA forensic evidence), the search would be more focused and may yield one to only a few possible matches. Comparison may be done manually or with the aid of a computer. One approach to implementing this method is to build upon existing directed subgraph matching or (partial) isomorphism search and retrieval methods. A search can identify isomorphic structures in the database corresponding (partially) to a target directed graph, and compare test DNA profile information to determine any candidate matches to target DNA profiles which lie within the defined neighborhoods, as shown in block 350. Multiple test DNA profiles in the database may match simultaneously within a stored directed graph structure, corresponding to multiple test DNA profile types corresponding to an unknown biological specimen and/or the test DNA profiles corresponding to multiple biological specimens associated by a subgraph that is at least partially isomorphic to the target directed graph, as shown in block 350. A second approach to implementing this method utilizes link discovery methods to discover clusters within the directed graph that is constructed as described herein. These clusters correspond to groups of related specimens and individuals and include the family pedigree information represented within the database. Link discovery methods can also be used to identify and visually inspect clusters of related nodes corresponding to individuals and/or remains.

One way in which this embodiment can be implemented is to construct a database that contains information about specimens and individuals. Note that a "database" may be implemented as a collection of databases or database tables, or it may be any other method of organized information storage. Each specimen or individual can be represented in the database as a node or database object, as this term is known in the literature, corresponding to a node of a directed graph. DNA and non-DNA information about each specimen or individual can be associated with this node using methods that are well known in the field of computer science. Known relationships between specimens or individuals can also be stored in the database and correspond to edges of a directed graph containing the nodes. A list of possible relationships between individuals or specimen can be maintained and defines the set of possible hypothetical relationships between specimen or individuals. For any pair of specimens or individuals represented in the database, a likelihood function value of each possible hypothetical relationship can be calculated based upon the information stored in the database, and this likelihood function value can be tested to determine if information about a hypothetical relationship between this pair of specimens or individuals should be stored in the database. If the result of this test determines that the hypothetical relationship should be stored or recorded, the hypothetical relationship can be recorded as an edge in the database with associated information including, for example, the hypothetical relationship and the likelihood that the hypothetical relationship is true. More than one hypothetical relationship may be recorded in this manner for any pair, although in many cases no hypothetical relationship will be recorded because the available information does not support the hypothesis that a relationship exists. In this manner, a database can be constructed that contains DNA and non-DNA information about specimens and individuals and their relationships and includes hypothetical relationships that are evaluated to be sufficiently likely to be true. The terms "likely" and "likelihood" may correspond to the mathematical definitions of likelihood functions or likelihood ratios from the fields of population genetics, statistics, or probability, but this is not necessary. Other functions that quantify the strength of a hypothetical relationship between two individuals or specimens relative to other hypothetical relationships may be used, such as probabilities, log likelihood functions, Or measures of genetic similarity such as the number of genetic markers in common, the relative lengths of two genetic sequences, or the edit distance between two genetic sequences.

An advantage of this method over existing methods is its ability to simultaneously hypothesize and record multiple possible relationships. A second advantage is that a specimen may be related to multiple family pedigrees through edges of the directed graph that correspond to accepted and recorded hypotheses. Thus, unlike previous methods, the specimens are not partitioned into disjoint subsets that are hypothetically related to a single family pedigree. Such a partitioning can result in classification errors, since at the partitioning step insufficient information is known to accurately perform the partitioning. An incorrect assignment of a specimen to a partition in this case would eliminate the possibility of correctly identifying the specimen's family pedigree at a later time. In contrast, the claimed method allows a specimen to hypothetically belong to more than one family pedigree, and subsequent mathematical analysis, such as by using a pedigree likelihood ratio, can be used to determine the correct family pedigree.

A family pedigree containing information about individuals and relationships can be used as a target for a query or search of this database to locate portions of the database that are likely to correspond to the structure and information provided by the family pedigree. Such correspondence can be further evaluated using a pedigree likelihood ratio such as a modified Elston Stewart algorithm or other quantitative evaluation of the degree of correspondence of that portion to the family pedigree, relative to other possible portions of the database. In this manner, multiple portions of the database, which can be described as subgraphs, can be identified as possibly corresponding to the family pedigree, and such portions can be rank ordered using, for example, a pedigree likelihood ratio. Since there may be ambiguity within each portion as to the relationships among individuals and samples, evaluations of multiple possible family pedigrees within this portion can be performed to determine the more likely family pedigrees, providing a method of identification of possible relationships among, for example, unidentified human remains, using methods that are well-known in the field of DNA forensics, similar to those used, for example, to analyze the mass grave containing the probable remains of the Romanov family.

An alternative method is to search first for DNA profiles with likely or probable genetic relationships, followed by a search for matching directed subgraphs to the target directed graph. Preferably, one would perform these searches simultaneously. One method for implementing this is to alternately resolve searches for potentially related DNA profiles and subgraph structures at each level of a database index structure, where each level successively reduces the set of possible matches to the target directed graph and DNA profiles within the database.

The process of discovering relationships among biological specimens can lead to the identification of at least two biological specimens with similar DNA profiles, suggesting that these specimens are derived from the same individual. Biological specimens with similar DNA profiles can be collapsed into one specimen to enhance the speed and efficiency of the search.

An advantage of the rapid advances over the past decades in available computational capabilities is that idle computational capability is either available during periods of reduced utilization, or can be made available through the addition of computational elements or partitioning of available computational resources among several tasks. A program can allocate these unused computational capabilities to background processes that do not have to perform in a time-critical environment. It is advantageous to utilize background processes, also referred to as "spiders," to examine stored data during idle periods, determine hypothetical relationships between samples and their corresponding DNA profiles stored in a database, perform analyses to assess the potential truth of these hypothetical relationships, and record edges in the database indicating the presence of these hypothetical relationships. Such relationships can subsequently form the basis for information that can be compared to target family pedigrees, or directed graphs representing those family pedigrees, and associated DNA profiles in order to achieve identification of unknown remains, associate such remains with missing individuals, and link these items to relatives. Such spiders, or background processes, can thus provide a substantial benefit by improving the accuracy, efficiency, and speed of identification of unknown biological specimens.

Information about unidentified human remains, known individuals, missing persons, and/or family pedigrees can be collected over a substantial period of time, such as several months to a few years. In this case, the method is applied in a continuous or intermittent manner over at least a portion of this period of time. As new information is added, spiders, or background processes, can evaluate hypothetical relationships between the new information and pre-existing information and record edges in the database indicating the presence of these hypothetical relationships. Such newly recorded relationships can subsequently form the basis for information that can be compared to target family pedigrees, or directed graphs, and associated DNA profiles in order to achieve new identification of unknown remains, associate these remains with missing individuals, and link these items to relatives. Both new information and the results of identifications can enable further identification. For example, identification of a second parent or sibling in a family can be used to assist in identification of additional siblings. New information can also lead to the exclusion of some possible identifications. For example, the identification of an unidentified human remain excludes the identification of this remain as originating from a different person.

The methods described by these embodiments can be either static or dynamic. The method is static if the method is applied at one time to a collection of information that has been gathered about two or more biological specimens from unknown remains, known individuals, and/or missing persons. It is more common for the method to be applied in a dynamic manner. In this case, information is gathered over a period of time and the method is applied in a continuous or intermittent manner over a least a portion of this period of time. New information is added over a time period that can be fairly long, such as several months to a few years, and identifications occur as enough data accumulate to support them. Both newly arrived data and the results of identifications can enable further identification. For example, identification of a second parent or sibling in a family can be used to assist in identification of additional siblings. Newly arrived data can also lead to the exclusion of some possible identifications. For example, the identification of an unidentified human remain excludes the identification of this remain as originating from a different person.

In any of the methods of the invention, in addition to DNA profile information, non-DNA forensic information can be used to filter or exclude a set of unknown biological specimens to include those which fit one or more requirements specific to the missing individual or to the family searching to find a missing individual. "Non-DNA forensic information" according to the present invention includes, but is not limited to, dental records, skin markings (e.g., tattoos, scars), X-ray images, time of specimen collection, place of specimen collection, fingerprints, and gender. For example, in a group of unknown biological specimens, there may be body parts that contain tattoos. If a family is searching for a missing individual and knows that the missing individual does not have a tattoo, for example, this piece of information could exclude any unknown biological specimens which have a tattoo regardless of how well the DNA profiles seem to be related. As a second example, skeletal or other anatomical features may provide gender information.

Non-DNA forensic information also can be used to confirm the identification of an unknown biological specimen. Non-DNA forensic information can either be stored in a database which also contains DNA profile information, or in a separate database. For example, a cluster of unknown biological specimens identified as likely belonging to a missing individual may contain a jawbone which includes teeth. After carrying out a search method of the present invention dental records from the missing individual can be used to verify that the identification is correct. It is preferred to exclude an unknown biological sample from the set of unknown biological samples after identification.

Implementation Mechanisms—Hardware Overview

Methods of the first embodiment and subsequent embodiments may be utilized in connection with computer readable media which may be provided for temporary or permanent storage in a personal computer or other computer known in the art. FIG. 4 is a block diagram that illustrates a computer system 500 upon which at least one embodiment of the invention may be implemented. Computer system 500 includes a bus 502 or other communication mechanism for communicating information, and at least one processor 504 coupled with bus 502 for processing information. Computer system 500 also includes a main memory 506, such as a random access memory ("RAM") or other dynamic storage device, coupled to bus 502 for storing information and instructions to be executed by processor 504. Main memory 506 also may be used for storing temporary variables or other intermediate information during execution of instructions to be executed by processor 504. Computer system 500 may further include a read only memory ("ROM") 508 or other static storage device coupled to bus 502 for storing static information and instructions for processor 504. A storage device 510, such as a magnetic disk, optical disk, solid-state memory, or the like, may be provided and coupled to bus 502 for storing information and instructions.

Computer system 500 may optionally be coupled via bus 502 to a display 512, such as a cathode ray tube ("CRT"), liquid crystal display ("LCD"), plasma display, television, or the like, for displaying information to a computer user. Alternatively, information may be delivered to a computer user or another computer system or computer program using a communication interface 518. An input device 514, including alphanumeric and other keys, may be coupled to bus 502 for communicating information and command selections to processor 504. An optional type of user input device is cursor control 516, such as a mouse, trackball, stylus, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane. Alternatively, information and command selections may be communicated to processor 504 using a communication interface 518. Optionally, separate communication interfaces may be used to deliver information to a computer user or another computer system or computer program, and to communicate information and command selections to processor 504.

The invention is related to the use of computer system 500 for identifying an unknown biological specimen as likely related to a family comprising at least a first and second family member. According to one embodiment of the invention, identifying an unknown biological specimen as likely related to a family comprising at least a first and second family member is provided by computer system 500 in response to processor 504 executing one or more sequences of one or more instructions contained in main memory 506. Such instructions may be read into main memory 506 from another computer-readable medium, such as storage device 510. Execution of the sequences of instructions contained in main memory 506 causes processor 504 to perform the process steps described herein. In alternative embodiments, hard-wired circuitry may be used in place of or in combination with software instructions to implement the invention. For example, a field-programmable gate array (FPGA) or application-specific integrated circuit (ASIC) may be used. Such a device can, for example, implement associative memory to aid in indexing, search, and retrieval of information stored in a database. A second example is use of a FPGA or ASIC to speed up calculation of a likelihood function used to rank specimens. Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks, solid state memories, and the like, such as storage device 510. Volatile media includes dynamic memory, such as main memory 506. Transmission media includes coaxial cables, copper wire and fiber optics, including the wires that comprise bus 502. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, solid-state memory, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read. Various forms of computer readable media may be involved in carrying one or more sequences of one or more instructions to processor 504 for execution.

Computer system 500 may also include a communication interface 518 coupled to bus 502. Communication interface 518 provides a two-way data communication coupling to a network link 520 that is connected to a local network 522. For example, communication interface 518 may be an integrated services digital network ("ISDN") card or a modem to provide a data communication connection to a corresponding type of telephone line. As another example, communication interface 518 may be a network card (e.g., and Ethernet card) to provide a data communication connection to a compatible local area network ("LAN") or wide area network ("WAN"), such as the Internet or a private network. Wireless links may also be implemented. In any such implementation, communication interface 518 sends and receives electrical, electromagnetic or optical signals that carry digital data streams representing various types of information. For example, a forensic investigation may require a data communication connection to a database comprising at least DNA profile data or other forensic information. A second example is use of one or more data communication connection(s) to access at least one database used to stare DNA and/or non-DNA information.

Network link 520 typically provides data communication through one or more networks to other data devices. For example, network link 520 may provide a connection through local network 522 to a host computer 524 or to data equipment operated by an Internet Service Provider or private network service provider ("ISP"). ISP in turn provides data communication services through a packet data communication network such as the worldwide network commonly referred to as the "Internet" 528 or a private network. An example of a private network is a secure data network linking law enforcement agencies and used for transmission of DNA and/or non-DNA information. Local network 522 and Internet 528 both use electrical, electromagnetic or optical signals that carry digital data streams. The signals through the various networks and the signals on network link 520 and through communication interface 518, which carry the digital data to and from computer system 500, are exemplary forms of carrier waves transporting the information.

Computer system 500 can send messages and receive data, including program code, through the network(s), network link 520 and communication interface 518. In the Internet example, a server 530 might transmit a requested code for an application program through Internet 528, host computer 524, local network 522 and communication interface 518. In accordance with the invention, one such downloaded application provides a method of identifying an unknown biological specimen as likely related to a family comprising at least a first and second family member.

The received code may be executed by processor 504 as it is received, and/or stored in storage device 510, or other tangible computer-readable medium (e.g., non-volatile storage) for later execution. In this manner, computer system 500 may obtain application code and/or data in the form of an intangible computer-readable medium such as a carrier wave, modulated data signal, or other propagated signal.

Computer system 500 can be configured using the methods of this invention to provide services across a network to forensic personnel having client computers capable of connection to the network. Such services can include assistance in identification of unidentified remains and storage of DNA and non-DNA information about known individuals and missing persons and their relationships, or a family pedigree. These services can also be provided to other software, located in either computer system 500 or a separate computer system connected by a network, network link, or communication interface to computer system 500. The services can be protected using methods of authentication and/or encryption that are known in the fields of computer science and computer security in order to ensure data are neither compromised nor disclosed and to trace all accesses to the data. The computer system 500 and other associated information storage and communication components can be protected using devices and methods that are known in the fields of computer science and computer security, such as with firewalls, physical access controls, power conditioning equipment, and backup or redundant power sources. The information stored by computer system 500 and computer-readable media can be further protected using backup or redundant information storage systems, such as those that are well-known in the art. Examples include tape storage systems and RAID storage arrays.

All patents, patent applications, and references cited in this disclosure are expressly incorporated herein by reference.

REFERENCES

F. Dudbridge. A survey of Current Software for Linkage Analysis, Human Genomics, Vol 1, (1), 2004, 63-65.

Soledad A. Fernandez, Rohan L. Fernando, Bernt Guldbrandtsen, Liviu R. Totir, Alicia L. Carriquiry. Sampling genotypes in large pedigrees with loops. Genet. Sel. Evol. 33 (2001)337-367

Howard D. Cash, Jonathon W. Hoyle, and Amy J. Sutton, "Development under extreme conditions: forensic bioinformatics in the wake of the World Trade Center disaster," genecodesforensics.com/news/CashHoyleSutton.pdf, 2003

C. Cannings, E. A. Thompson, and H. H. Skolnick. The Recursive Derivation of Likelihoods on Complex Pedigrees. Advances in Applied Probability, Vol 8, No 4. (December 1976), pp 622-625.

E. Lander, and P Green. Construction of Multilocus Genetic Linkage Maps in Humans. PNAS, Vol 84, No. 8 (Apr. 15, 1987), pp. 2363-2367.

R. C. Elston and J. Stewart. A General Model for the Genetic Analysis of Pedigree Data. Human Heredity 21: 523-542 (1971).

An alphabetic list of Genetic Analysis Software is available from the North Shore Long Island Jewish Research Institute in New York.

What we claim is:

1. A computer-implemented method of identifying an unknown biological specimen as hypothetically related to a family pedigree comprising at least a missing person and relationships to at least two family members having genetic information for use in a system, the system comprising a processor, a memory connected to the processor, an input for receiving a DNA profile and an output device, the computer-implemented method comprising:
   (a) pre-computing, via the computer processor, a portion of a pedigree likelihood ratio that a specified genetic relationship exists between a set of unknown biological specimens of a missing person and said at least two family members of the family pedigree, said family pedigree being stored in said memory and said genetic information obtained from known biological specimens of said at least two family members;
   (b) comparing, via the computer processor, at least three test DNA profiles obtained from the set of unknown biological specimens of the missing person to the family pedigree, a DNA profile comprising at least one DNA marker;
   (c) using said pre-computed pedigree likelihood ratio portion and a modified Elston Stewart algorithm, via the computer processor, to calculate a pedigree likelihood ratio that a specified genetic relationship exists between at least one unknown biological specimen of the set of unknown biological specimens and said at least two family members of the family pedigree;
   (d) producing a resultant set of unknown biological specimens rank-ordered according to the pedigree likelihood ratio for the family pedigree via the output device; and
   (e) identifying an unknown biological specimen from the rank-ordered set with a high pedigree likelihood ratio as likely corresponding to said missing person belonging in the family pedigree.

2. The method of claim 1 wherein family pedigree members' profiles comprise two DNA types selected from the group consisting of:
   a) STR;
   b) partial STR;
   c) Y-STR;
   d) SNP;
   e) mini-STR; and
   f) mitochondrial DNA.

3. The method of claim 1 wherein comparing further comprises excluding a biological specimen not compatible with the family pedigree.

4. The method of claim 1 wherein said DNA profiles obtained from the set of unknown biological specimens and genetic information about said at least two family pedigree members' profiles are stored in a database.

5. The method of claim 4 wherein the database comprises non-DNA forensic information which describes at least one unknown biological specimen.

6. The method of claim 4 wherein a DNA profile or non-DNA forensic information is used to exclude an unknown biological specimen from the resultant set of unknown biological specimens to form an updated database.

7. The method of claim 4 further comprising adding an unknown biological specimen to the set of unknown biological specimens of the database to form an updated database.

8. The method of claim 7 further comprising applying the computer-implemented method to the updated database.

9. The method of claim 4 wherein the family pedigree comprises two generations, the method comprising
   pre-computing the likelihood ratio portion in a recursive manner in one of a bottom-up manner from the youngest available generation up and a top-down manner from the oldest available generation down.

10. The method of claim 7 further comprising associating a test DNA profile with the added unknown biological specimen, the method comprising:
    (a) comparing the associated test DNA profile to a family pedigree comprising target DNA profiles obtained from biological specimens of family members;
    (b) using an algorithm to calculate a pedigree likelihood ratio that a specified genetic relationship exists between the associated test DNA profile and the family pedigree; and
    (c) identifying or excluding the added unknown biological specimen of the resultant set as likely related to the family pedigree based on the pedigree likelihood ratio.

11. The method of claim 1 further comprising using non-DNA forensic information to confirm identification of the unknown biological specimen.

12. The method of claim 11 wherein the non-DNA forensic information comprises at least one type selected from the group consisting of:
    a) a dental record;
    b) a skin marking;
    c) an X-ray image;
    d) a time of specimen collection;
    e) a place of specimen collection; and
    f) a fingerprint.

13. The method of claim 1 wherein pre-computing comprises computing a product term for available siblings of the family pedigree, the available siblings comprising the at least two family members of the family pedigree.

14. A computer-readable medium storing computer-executable instructions for performing a computer-implemented method of identifying an unknown biological specimen as hypothetically related to a family pedigree comprising at least a missing person and relationships to at least two family members having genetic information for use in a system, the system comprising a processor, a memory connected to the processor, an input for receiving a DNA profile and an output device, the computer-implemented method comprising:
    (a) pre-computing, via the computer processor, a portion of a pedigree likelihood ratio that a specified genetic relationship exists between a set of unknown biological specimens of a missing person and said at least two family members of the family pedigree, said family pedigree being stored in said memory and said genetic information obtained from known biological specimens of said at least two family members;

(b) comparing, via the computer processor, at least three test DNA profiles obtained from the set of unknown biological specimens of the missing person to the family pedigree, a DNA profile comprising at least one DNA marker;

(c) using said pre-computed pedigree likelihood ratio portion and a modified Elston Stewart algorithm, via the computer processor, to calculate a pedigree likelihood ratio that a specified genetic relationship exists between at least one unknown biological specimen of the set of unknown biological specimens and said at least two family members of the family pedigree;

(d) producing a resultant set of unknown biological specimens rank-ordered according to the pedigree likelihood ratio for the family pedigree via the output device; and (e) identifying an unknown biological specimen from the rank-ordered set with a high pedigree likelihood ratio as likely corresponding to said missing person belonging in the family pedigree.

15. The computer readable medium of claim 14 wherein comparing further comprises excluding an available or unknown biological specimen not compatible with the family pedigree.

16. The computer-readable medium of claim 14 wherein the at least two test DNA profiles comprise two DNA types selected from the group consisting of:
 a) STR;
 b) partial STR;
 c) Y-STR;
 d) SNP;
 e) mini-STR; and
 f) mitochondrial DNA.

17. The computer-readable medium of claim 14 wherein said DNA profiles from the set of unknown biological specimens and family pedigree data and genetic information obtained from biological specimens of said at least two family members are stored in a database.

18. The computer readable medium of claim 17 wherein the DNA profiles, family pedigree data and said genetic information are stored in a plurality of databases.

19. The computer-readable medium of claim 17 wherein the database comprises non-DNA forensic information which describes at least one unknown biological specimen.

20. The computer-readable medium of claim 17 wherein a DNA profile or non-DNA forensic information is used to exclude an unknown biological specimen from the resultant set of unknown biological specimens to form an updated database.

21. The computer-readable medium of claim 17 wherein the method further comprises adding an unknown biological specimen to the database to form an updated database.

22. The computer-readable medium of claim 21 further comprising associating a test DNA profile with the added unknown biological specimen and applying the computer-implemented method to the updated database.

23. The computer-readable medium of claim 14, the method comprising repeating:
 (a) adding a DNA profile obtained for a different unknown biological specimen to the set of unknown biological specimens;
 (b) comparing an added DNA profile for the different unknown biological specimen to a family pedigree comprising target DNA profiles obtained from biological specimens of family members;
 (b) using the pre-computed likelihood ratio portion and an algorithm to calculate, via the computer processor, a pedigree likelihood ratio that a specified genetic relationship exists between at least one unknown biological specimen and the family pedigree; and
 (c) updating said resultant set of unknown biological specimens rank-ordered according to the pedigree likelihood ratio.

24. The computer readable medium of claim 23 further comprising identifying an unknown biological specimen from the rank-ordered resultant set as a missing person of the family pedigree and subsequently identifying a second unknown biological specimen as likely related to the missing person of the family pedigree.

25. The computer readable medium of claim 24 where the second unknown biological specimen is identified as a sibling of said missing person.

26. The computer readable medium of claim 21 further comprising associating a test DNA profile with the added unknown biological specimen, the method comprising:
 (a) comparing the associated test DNA profile to a family pedigree comprising target DNA profiles obtained from biological specimens of the at least two family members;
 (b) using an algorithm to calculate a pedigree likelihood ratio that a specified genetic relationship exists between the associated test DNA profile and the family pedigree; and
 (c) identifying or excluding the added unknown biological specimen of the resultant set as likely related to the family pedigree based on the pedigree likelihood ratio.

27. The computer-readable medium of claim 19 wherein non-DNA forensic information is utilized and the non-DNA forensic information comprises at least one type selected from the group consisting of:
 a) a dental record;
 b) a skin marking;
 c) an X-ray image;
 d) a time of specimen collection;
 e) a place of specimen collection; and
 f) a fingerprint.

28. The computer-readable medium of claim 14 wherein the said at least three test DNA profiles are neither excluded nor identified as likely related to the family pedigree based on the pedigree likelihood ratio.

29. A computer having a processor, a memory and an output device for performing a computer-implemented method of identifying an unknown biological specimen as hypothetically related to a family pedigree comprising a missing person and at least a first, a second and a third family member, the method comprising:
 (a) pre-computing, via the computer processor, a portion of a pedigree likelihood ratio that a specified genetic relationship exists between a set of unknown biological specimens of a missing person and said at least two family members of the family pedigree, said family pedigree being stored in said memory and said genetic information obtained from known biological specimens of said at least two family members;
 (b) comparing, via the computer processor, at least three test DNA profiles obtained from the set of unknown biological specimens of the missing person to the family pedigree, a DNA profile comprising at least one DNA marker;
 (c) using said pre-computed pedigree likelihood ratio portion and using a modified Elston Stewart algorithm, via the computer processor, to calculate a pedigree likelihood ratio that a specified genetic relationship exists between at least one unknown biological specimen of the set of unknown biological specimens and said at least two family members of the family pedigree;

(d) producing a resultant set of unknown biological specimens rank-ordered according to the pedigree likelihood ratio for the family pedigree via the output device; and (e) identifying an unknown biological specimen from the rank-ordered set with a high pedigree likelihood ratio as likely corresponding to said missing person belonging in the family pedigree.

30. The computer of claim 29 wherein the at least two test DNA profiles comprise two DNA types selected from the group consisting of:
   a) STR;
   b) partial STR;
   c) Y-STR;
   d) SNP;
   e) mini-STR; and
   f) mitochondrial DNA.

31. The computer of claim 29 wherein the at least three test DNA profiles and the family pedigree members' DNA profiles are stored in a database.

32. The computer of claim 31 wherein the database comprises non-DNA forensic information which describes at least one unknown biological specimen of the set of unknown biological specimens, the non-DNA forensic information comprising one of dental data, tattoo data, scar data, and a date of specimen collection.

33. The computer of claim 32 wherein a DNA profile or non-DNA forensic information is used to exclude an unknown biological specimen from the set of unknown biological specimens to form an updated database.

34. The computer of claim 32 further comprising adding an unknown biological specimen to the set of unknown biological specimens of the database to form an updated database.

35. The computer of claim 34 for implementing a method further comprising applying the computer implemented method to the updated database.

36. The computer of claim 31 wherein the family pedigree comprises two generations, the method comprising repeating:
   (a) comparing said at least three test DNA profiles from a set of unknown biological specimens to a family pedigree comprising target DNA profiles obtained from biological specimens of family members;
   (b) using an algorithm to calculate a likelihood function value that a genetic relationship exists between at least one unknown biological specimen and the family pedigree; and
   (c) excluding an unknown biological specimen having a small likelihood function value as likely related to the family.

37. The computer of claim 31 wherein the family pedigree comprises two generations, the method comprising repeating:
   (a) comparing said at least three test DNA profiles to a family pedigree comprising target DNA profiles obtained from biological specimens of family members;
   (b) using an algorithm to calculate a pedigree likelihood ratio that a specified genetic relationship exists between the test DNA profiles of, the set of unknown biological specimens and the family pedigree; and
   (c) either identifying or excluding said at least two test DNA profiles as likely related with the specified genetic relationship to the family pedigree based on the pedigree likelihood ratio.

38. The computer of claim 35 further comprising associating a test DNA profile with the added unknown biological specimen, the method comprising:
   (a) comparing the associated test DNA profile to a family pedigree comprising target DNA profiles obtained from biological specimens of family members;
   (b) using an algorithm to calculate a pedigree likelihood ratio that a specified genetic relationship exists between the associated test DNA profile and the family pedigree; and
   (c) identifying or excluding the added unknown biological specimen of the set of unknown biological specimens as likely related with the specified genetic relationship to the family pedigree based on the pedigree likelihood ratio.

39. The computer of claim 36 wherein the likelihood function value comprises a pedigree likelihood ratio and the first and second family members comprise two different family members selected from a group comprising a father, a mother, a child and a sibling of the missing person.

40. The computer of claim 36 wherein the likelihood function value comprises a probability measure for a degree of linkage of markers residing at different loci.

* * * * *